(12) United States Patent
Preuss et al.

(10) Patent No.: US 12,099,259 B2
(45) Date of Patent: Sep. 24, 2024

(54) LENS ELEMENT AND CONTACT APPARATUS FOR AN OPHTHALMOLOGICAL LASER THERAPY SYSTEM

(71) Applicant: CARL ZEISS MEDITEC AG, Jena (DE)

(72) Inventors: Dirk Preuss, Jena (DE); Beate Böhme, Großpürschütz (DE); Gregor Stobrawa, Jena (DE); Andreas Wirth, Simbach am Inn (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 779 days.

(21) Appl. No.: 17/271,862

(22) PCT Filed: Sep. 2, 2019

(86) PCT No.: PCT/EP2019/073347
§ 371 (c)(1),
(2) Date: Feb. 26, 2021

(87) PCT Pub. No.: WO2020/048920
PCT Pub. Date: Mar. 12, 2020

(65) Prior Publication Data
US 2021/0318555 A1 Oct. 14, 2021

(30) Foreign Application Priority Data

Sep. 4, 2018 (DE) ...................... 10 2018 215 030.3

(51) Int. Cl.
*G02C 7/04* (2006.01)
*A61F 9/009* (2006.01)
(52) U.S. Cl.
CPC .............. *G02C 7/049* (2013.01); *A61F 9/009* (2013.01); *G02C 7/047* (2013.01)

(58) Field of Classification Search
CPC ......... G02C 7/049; G02C 7/047; A61F 9/009; A61F 9/008; A61F 9/00; A61F 9/0008;
(Continued)

(56) References Cited

U.S. PATENT DOCUMENTS

2003/0043728 A1 3/2003 Kan et al.
2004/0174618 A1 9/2004 Kikuchi
(Continued)

FOREIGN PATENT DOCUMENTS

DE            103 54 025 A1     6/2005
DE      10 2005 040 338 A1     3/2007
(Continued)

OTHER PUBLICATIONS

International Search Report for PCT/EP2019/073347 mailed Jan. 16, 2020, 6 pages.
(Continued)

*Primary Examiner* — Travis S Fissel
(74) *Attorney, Agent, or Firm* — DeWitt LLP

(57) ABSTRACT

A lens element and a one-piece contact apparatus having a lens element and a holding device for fixing a patient's eye to a laser applicator of an ophthalmological laser therapy system and a corresponding production method. The production method is conceptually simple and user-friendly and allows a high degree of automation while at the same time meeting the high requirements for mechanical and optical precision of the lens element. The lens element has an optically effective zone and a joining zone. The joining zone also has a functional zone for joining the lens element to a holding device which is arranged continuously circumferentially or interrupted circumferentially at the outer edge of the lens element. The contact apparatus includes a lens element and a holding device, which are permanently connected to one another, wherein the lens element and the
(Continued)

holding device are not connected to one another by adhesive-bonding.

19 Claims, 6 Drawing Sheets

(58) Field of Classification Search
CPC .. A61F 9/0017; A61F 9/0026; A61F 9/00802; A61F 9/00804; A61F 9/00806; A61F 9/00808; A61F 9/00812; A61F 2009/00885; A61F 2009/0088
USPC ... 351/200, 159.02, 205, 207, 209, 245, 216
See application file for complete search history.

(56) References Cited

U.S. PATENT DOCUMENTS

| | | | |
|---|---|---|---|
| 2007/0156079 | A1 | 7/2007 | Brown |
| 2007/0237620 | A1 | 10/2007 | Mühlhoff et al. |
| 2009/0244477 | A1 | 10/2009 | Pugh et al. |
| 2010/0228236 | A1* | 9/2010 | Muhlhoff ............... A61B 90/30 606/4 |
| 2014/0216468 | A1 | 8/2014 | Goldshleger et al. |
| 2014/0276673 | A1* | 9/2014 | Heitel ..................... A61F 9/008 606/4 |
| 2018/0235594 | A1* | 8/2018 | Scheller ................. A61B 17/30 |

FOREIGN PATENT DOCUMENTS

| | | |
|---|---|---|
| DE | 10 2017 215 589 A1 | 3/2019 |
| EP | 1 208 792 A1 | 5/2002 |
| EP | 1 844 745 A2 | 10/2007 |
| WO | WO 02/39892 A1 | 5/2002 |
| WO | WO 2007/022993 A2 | 3/2007 |
| WO | WO 2009/123985 A1 | 10/2009 |
| WO | WO 2010/066521 A2 | 6/2010 |
| WO | WO 2013/162724 A1 | 11/2013 |
| WO | WO 2013/167274 A1 | 11/2013 |
| WO | WO 2014/127242 A2 | 8/2014 |
| WO | WO 2015/136520 A1 | 9/2015 |
| WO | WO 2018/049246 A1 | 3/2018 |

OTHER PUBLICATIONS

English translation of International Search Report for PCT/EP2019/073347 mailed Jan. 16, 2020, 3 pages.
Written Opinion of the ISA for PCT/EP2019/073347 mailed Jan. 16, 2020, 8 pages.
English translation of Written Opinion of the ISA for PCT/EP2019/073347 mailed Jan. 16, 2020, 8 pages.
International Preliminary Report on Patentability for Written Opinion of the ISA for PCT/EP2019/073347 mailed issued Mar. 9, 2021, 9 pages.
English translation of International Preliminary Report on Patentability for Written Opinion of the ISA for PCT/EP2019/073347 mailed issued Mar. 9, 2021, 9 pages.
International Search Report for PCT/EP2019/055440, mailed Jan. 16, 2019, 6 pages.
Written Opinion for PCT/EP2019/055440, mailed Jan. 16, 2019, 20 pages.
English translation of Written Opinion for PCT/EP2019/055440, mailed Aug. 19, 2019 11 pages.
IPRP for PCT/EP2019/055440, mailed Jan. 16, 2019, 12 pages.

* cited by examiner

LENS ELEMENT AND CONTACT APPARATUS FOR AN OPHTHALMOLOGICAL LASER THERAPY SYSTEM

RELATED APPLICATIONS

This application is a National Phase entry of PCT Application No. PCT/EP2019/073347 filed Sep. 2, 2019, which application claims the benefit of priority to DE Application No. 10 2018 215 030.3 filed, Sep. 4, 2018, the entire disclosures of which are incorporated herein by reference.

BACKGROUND

The present invention relates to a lens element for a contact apparatus and to a one-piece contact apparatus having a lens element and a holding device for fixing the relative geometrical position of a patient's eye with respect to a laser applicator of an ophthalmological laser therapy system. The present invention further relates to corresponding production methods of the lens element and the contact apparatus. In order to focus laser radiation on a patient's eye, in particular on the cornea, but also on deeper structures such as the lens, during eye treatments, it is necessary to create a stable spatial relationship between the focus position of the laser beam and the patient's eye. This means that there must be a stable spatial or positional relationship to the exit location of the focused laser radiation from an ophthalmological laser therapy system, the laser applicator. Since the patient's eye usually moves (at least microsaccades cannot easily be prevented), this either requires a powerful tracking system that can guide the laser focus to follow the eye movements immediately and precisely, or fixation of the patient's eye to the ophthalmological laser therapy system. Such a fixation is usually carried out by a contact element or a contact apparatus, which fixes the patient's eye and is attached to the laser therapy system.

Such a contact apparatus, also called a patient interface, can be designed as a liquid patient interface, in which a volume between a lens element and the patient's eye is filled with a physiological salt solution (BSS, buffered salt solution), which prevents a significant deformation of the patient's eye during the suction operation of the patient interface and at the same time causes an adjustment of the refractive index in the space between the lens element and the patient's eye. A liquid patient interface is necessary especially when the laser radiation is to be focused into deeper structures of the eye.

To process the cornea, however, a lens element is usually used that lies directly against the cornea of the patient's eye. Such a contact apparatus is also called a contact glass. It has a significantly simpler construction than a liquid patient interface, since filling of a volume between the lens element and the patient's eye is not necessary in this case and a suction device and its volume do not have to be separated from the liquid-receiving volume either.

However, in any contact apparatus, the part of the contact apparatus through which the focused laser radiation is to be directed into the patient's eye, i.e. the optically effective zone of the lens element, must allow the radiation to be focused, and, if possible, no disruptive interactions with the lens element, as a result of which the latter heats up, for example, must arise. In order to support the focusing of the laser radiation, it must be manufactured geometrically very precisely. Therefore, there are special optical requirements for the optically effective zone of the contact apparatus.

In the prior art, see for example the contact apparatus or the contact glass in document WO 2007/022993 A2, the lens element is made from a mineral glass (glass lens). This makes possible the highest possible optical quality, in particular with respect to the homogeneity of the refractive index, the surface quality, the inclusions, etc.

The manufacturing complexity is very high in this regard. Even if the remaining part of the contact apparatus, i.e. the holding device, which comprises a wall, a lower suction element, and a vacuum feed-through (for a holding apparatus of a liquid patient interface, it furthermore comprises a filling channel for the physiological salt solution), is produced by a simple manufacturing method, such as plastic injection molding, there arises the need to join at least two pieces in order to obtain a one-piece contact apparatus.

Such a one-piece contact apparatus offers the physician (user) the advantage that the use of this contact apparatus to fix the relative geometric position of the patient's eye with respect to the laser applicator of an ophthalmological laser therapy system is much easier because it can be fixed with one hand. In multi-part contact apparatuses, the physician usually needs both hands to assemble said parts during use. In addition, work should be carried out as sterile as possible at this point. A reproducible positioning ability is also less reliable in the case of multi-part contact apparatuses.

According to the prior art, in order to obtain a one-piece contact apparatus, the lens element is therefore adhesively bonded into the holding device (also called a contact glass holder in the case of a contact glass) by use of UV adhesive. The adhesive is applied either manually or automatically. The curing takes place in a UV curing oven. The method of adhesively bonding the lens is very time-consuming and can be automated only to a limited extent and with great effort, since several handling steps are required.

Such adhesive-bonding methods are thus complex and associated with a process stability that is controllable only with great effort. The adhesive-bonding methods are always subject to a special validation and risk assessment and are therefore also relevant for approval.

In addition, as already indicated above, the manufacturing of the lens elements from glass (glass lenses) is a multi-stage process that requires a lot of time and personnel. The maximum manufacturing capacity for lens manufacturing is limited by the use of tools and personnel available. Long-term investments and the lack of qualified personnel stand in the way of a rapid expansion of the manufacturing capacities. Complex optical test methods for guaranteeing consistent quality are also associated with the manufacturing of lens elements made from glass.

It is therefore the object of the present invention to describe a lens element and a one-piece contact apparatus whose production method is conceptually simple and user-friendly, allows a high degree of automation, and allows the problem-free expansion of manufacturing capacities while at the same time meeting the high requirements for technical (mechanical and also optical) precision of the lens element.

To achieve the object, it is necessary to consider material-related and geometric aspects as well as procedural aspects.

In addition to the adhesive-bonding methods used in the prior art for permanently bonding the lens element to the holding device, there are of course other joining methods, described below, which have not yet been used for the reasons that will likewise be mentioned here:

Contact apparatuses produced with the one-component injection molding method (1K) are not possible due to the complexity of the overall geometry of the contact apparatus made of a lens element in combination with the holding device, in order to manufacture a contact apparatus that meets the optical and the mechanical requirements for the lens element. In such a one-component injection molding method, maybe the lens element can be manufactured, possibly together with a very simple part of the holding device, and then has to be connected to the holding device or the rest of the holding apparatus by use of another joining method.

In the two-component injection molding method (2K), an element is injection-molded from a component A, and this injection-molded element is overmolded by or injection-molded in a component B in the same tool in a subsequent injection molding process. However, this involves a renewed melting of the material of component A at the joining surface, and the optical parameters of the element of component A (for example the lens element), which were attained with very high accuracy by way of the process control of the injection molding, in particular a corresponding control of the pressure, the temperature, and the cooling regime of the element of component A, significantly worsen in the vicinity of the joining surface by the injection molding of component B.

When an existing lens element made from glass or plastic is overmolded, it is received in the injection molding tool and overmolded with a component B having a geometry that corresponds to the geometry of the holding device. However, melting of the lens element, or at least remelting of the lens element on its surface, may occur even in this case, which can lead, for example, to a change in shape or a permanent application of force (mechanical stress) and thus to the optical properties worsening at least in those surface regions.

In laser welding and ultrasonic welding, joining takes place by heating parts lying against one another using local, focused laser irradiation or ultrasonic waves, which causes the parts to melt and connect. However, as far as the lens element is concerned, the melting of the material in the region of the optically effective zone causes the loss of optical quality.

In the case of snap connections (click connections), a type of mechanical connection, the elements to be connected must be designed in such a way that elastic deformation of at least one of the components results in a form fit during the joining process. At the contact location between the two elements, however, mechanical stresses are usually permanently introduced into the material when they are connected, and the mechanical stresses may change the refractive index. When using plastics lenses, which in terms of shape make such a design easier than a lens element made from glass, the stress-induced change in the refractive index is may be particularly pronounced.

In pressing connections, an alternative type of mechanical connection, the lens element must be manufactured with a slight undersize, with an exact fit, or with an oversize with respect to the holding device. The connection is made by pressing in, wherein the softer material presses around the harder material, thus creating a force-fit connection. This method also introduces mechanical stresses into the lens element. This is particularly pronounced when the difference in material hardness is small (for example in the case of a plastics lens in a plastics frame), which, as already described, can cause stress-induced changes in the refractive index, in particular stress birefringence.

All commonly used joining methods therefore have a more or less negative influence on the optical properties. This can already be observed in lens elements made from glass, but becomes much more critical in plastics lens elements because of the low hardness of the material of these polymer optics. For this reason, a process of adhesively bonding lens elements made from glass into a holding apparatus made from plastic is currently state of the art.

It is therefore the object of the present invention, in particular, to describe a lens element and a one-piece contact apparatus whose production method is conceptually simple and user-friendly, allows a high degree of automation, which allows a problem-free expansion of manufacturing capacities while at the same time meeting the high requirements for mechanical and also optical precision of the lens element, and overcomes the problems discussed above.

SUMMARY OF THE INVENTION

A lens element for a contact apparatus, which has a lens element and a holding device and is used to fix the relative geometric position of a patient's eye with respect to a laser applicator of an ophthalmological laser therapy system, has an optically effective zone and a joining zone with a joining surface. A joining zone is the zone via which the lens element and the holding device are joined together, i.e. in which there is contact between the lens element and the holding device of the contact apparatus. The joining surface is a part of the boundary of the joining zone. As a rule, however, it does not extend over the entire outer boundary of the joining zone, but can even be limited to a very point-type region. The joining zone or the joining process must be designed in such a way that the joining does not have any negative effects on the optical and mechanical quality of the optically effective zone of the lens element beyond the joining zone.

According to the invention, such a lens element is characterized in that the joining zone of the lens element further comprises a functional zone for joining the lens element in a holding device which is arranged continuously circumferentially or discontinuously circumferentially at the outer periphery of the lens element.

The functional zone is therefore a "consumption zone," in which material can be changed or indeed removed in the subsequent joining process and which is now additionally assigned to the joining zone. It is used as a buffer zone for the consumption or conversion during the joining, in which optical and mechanical properties can thus be changed by the joining process without the optically effective zone of the lens element being influenced.

This functional zone prevents the optically effective zone from being restricted in the subsequent joining method or any other connecting method for the lens element and the holding device, in particular if the connection is to be made without an adhesive-bonding process but by one of the joining processes described above.

For the remainder, when there is no functional zone, the joining surface is part of the periphery of the original lens element. An additional functional zone of the joining zone, on the other hand, would allow the joining surface and periphery of the original lens element to fall apart if the entire functional zone is not used up during joining.

In the specific implementation of the functional zone, its geometry and thus ultimately the geometry of the entire lens element according to the invention is selected in such a way that the negative properties of the selected joining process lie in the optically irrelevant region—i.e. occur only in the joining zone (extended by the functional zone), wherein in particular changes in shape and fundamental qualitative changes in the physical properties of the lens element are intended only for the functional zone. In an example lens element according to the invention, the functional zone accordingly comprises a joining contact zone, which is provided for remelting or injection-molding for the permanent connection of the lens element to a holding device, or a melt lip, which is provided for laser-welding or ultrasonic welding a holding device in order to permanently connect the holding device and lens element to form a one-piece contact apparatus, or an undercut for effecting a click connection with a holding device.

In an advantageous example lens element according to the invention, either the optically effective zone and the functional zone of the lens element are made in a single piece from a mineral glass, i.e. an optical glass, for example made from silicon dioxide, or the optically effective zone and the functional zone of the lens element are made, in particular in a single piece, from a polymer, or the optically effective zone of the lens element is made from a mineral glass and the functional zone of the lens element is made from a polymer.

In the following, the term "one-piece" means that all parts of the contact apparatus are permanently connected to one another, so that assembly in the operation room (OR) before the contact apparatus is used, as is common with many other models of such contact apparatuses, is unnecessary, and the contact apparatus can be used by the user without any further assembly in order to fix the relative position of a patient's eye with respect to a laser applicator of an ophthalmological laser therapy system. In this way, the use of this contact apparatus is possible even without help by an assistant, and the configuration complexity prior to an OR surgery is very low.

The use of the term "single-piece" refers to the manner of production: It characterizes manufacturing of the respective element "from one single piece" or "in one single piece." Two successive injection molding steps in which there is no reloading after the first step should still fall under the term "single-piece" here.

The optical material of the lens element, regardless of whether it is mineral glass or polymer, must offer high transparency for the therapy (laser) wavelengths, but also for the wavelengths of examination radiation (e.g. OCT wavelengths). If used in refractive surgery, pulsed laser radiation, typically from a femtosecond laser source or a picosecond laser source, is usually used as the therapy laser radiation. Typical examination wavelengths, in turn, are all wavelengths used in optical coherence tomography, but also the wavelengths of visible light and infrared radiation. The choice of material is therefore limited by the requirements placed on the refractive index of the optically effective zone with respect to this radiation.

In a special design of the lens element according to the invention, it comprises a part of a holding device, in particular a suction element. The lens element and the part of the holding device are in this case manufactured together using the one-component injection molding method.

A contact apparatus is used to fix the relative geometric position of a patient's eye with respect to a laser applicator of an ophthalmological laser therapy system, which usually includes a laser source, in particular a femtosecond or a picosecond laser source, a scanning unit, which can comprise a plurality of scanners, for scanning the laser beam generated by the laser source, a focusing optical unit for focusing the laser beam, and a control unit, which in turn can comprise a multiplicity of individual controllers, and optionally various examination units, such as an optical coherence tomograph (OCT), a confocal detector, a slit lamp, an ultrasonic unit and/or a surgical microscope.

Such a contact apparatus comprises a lens element and a, for example, frustoconical holding device, which are permanently connected to one another, with the result that the contact apparatus is made in one piece. The lens element has an optically effective zone, in particular having a lens function, a joining zone having a joining surface and a circumferential peripheral region of a constant thickness that is not equal to zero, which peripheral region allows direct contact with—and thus a direct connection to—the laser applicator of the ophthalmological laser therapy system. The holding device comprises a wall, a lower suction element, and a vacuum feed-through, wherein the vacuum feed-through extends through the wall into the suction element.

According to the invention, the lens element and holding device are now permanently connected to one another, but not by use of an adhesive-bonding method: The lens element and/or the holding device are set up to be permanently connected to one another with the aid of another joining method. For this purpose, both the lens element and the holding device can be prepared by way of special designs, including geometric ones, for example with a corresponding shoulder in the holding device that makes it easier to align the lens element and holding device before the start of the joining process, or with consumption zones on the lens element and/or holding device that are used up in the joining process.

The relative position of the holding device with respect to the lens element is not critical in this case due to the design of the contact apparatus described here: Due to the direct contact and the possible direct connection of the lens element with the laser applicator, all critical requirements relating to manufacturing accuracy, i.e., to optical and mechanical parameters in the lens element, have been addressed. In fact, the one-piece holding device thereby opens up new ways of performing the joining process in a different manner than by way of an adhesive-bonding method. By contrast, if the contact apparatus were to be coupled to the laser applicator via the holding device, the lens element would, in turn, have to be connected to the holding device in a mechanically defined fashion and with very high precision. The result would then be an additional interface with very tight tolerance limits.

The lens element is here made from a mineral glass or a polymer, in particular using an injection molding method. The above statements made with respect to the material properties of the lens element also apply here.

The holding device is for example formed from a polymer. If the lens element is likewise formed from a polymer, the lens element and the holding device can be formed from the same polymer or from different polymers, in particular different polymers having different optical transparencies or different hardnesses.

A particularly advantageous example contact apparatus according to the invention has a lens element as described above.

In an example contact apparatus according to an embodiment of the invention, the lens element is permanently connected to the holding device, the geometry of which for this purpose can likewise be adapted to the joining method like that of the lens element, by use of one of the following methods, which are generally referred to as joining methods:

2-component injection molding method, overmolding, laser welding or ultrasonic welding, click connection,
pressing connection.

All of these methods are efficient, low-risk joining methods with which there is no need to use adhesive bonding as a joining method in production. The possibility of using polymer lens elements possibly eliminates efforts in qualifying glass suppliers, in particular if there is a need to increase production significantly. The manufacturing process is simplified and can be automated much better. And last but not least, such a concept of the contact apparatus offers the very important possibility of optical inline inspections, in particular optical inline inspections that can be integrated into an automated manufacturing process and no longer have to be carried out manually.

Furthermore, a contact apparatus according to the invention is for example one whose lens element and holding device are made from one or more materials
that do/does not include any substances that have a hormonal or hormone-like effect on the human organism, and/or
that are biocompatible.

A contact apparatus whose lens element is formed in a single piece is of great advantage.

In an advantageous example contact apparatus according to the invention, the lens element and holding device are manufactured additively in one process step.

Another example contact apparatus according to the invention has a connection between the lens element and the holding device over the entire circumference of the lens element.

The geometry of an advantageous example contact apparatus according to the invention is designed in such a way that an optical quality check is possible after connecting the lens element and the holding device, and optical controls, in particular automated optical inline inspections, are possible at any time.

It is furthermore advantageous for example if the contact apparatus is designed in such a way that (visible) light can be coupled in via the holding device for illuminating the patient's eye, in particular during laser therapy, when the patient's eye is fixed to/at the ophthalmological laser therapy system by application of the contact apparatus. A correspondingly polished region in the upper or side peripheral region of the wall of the holding device is helpful for this, for example, which can contact a corresponding light output coupling apparatus at the laser applicator of the ophthalmological laser therapy system. For this purpose, optical waveguides can for example be brought up to the contact apparatus, in particular to the holding device, at different locations of the contact apparatus.

In an advantageous example lens element according to the invention or an advantageous example contact apparatus according to the invention, the optically effective zone and/or possibly the functional zone is made from an optical polymer that has a refractive index close to that of mineral glass, in particular has a refractive index of between 1.4 and 1.55 for a wavelength of therapy laser radiation, for example manufactured by use of an injection molding method. One of the following example polymers is particularly beneficial here: polycarbonate, polystyrene, polymethyl methacrylate, cycloolefin polymers, cycloolefin copolymers, polyetherimide, polyethylene terephthalate, polysulfone.

Polymer lens elements can be produced in large numbers and cheaply, e.g., by an injection molding method. Here, the geometric form to be molded is converted into a mold as a negative. As a rule, this mold consists of chemically stable and dimensionally stable materials, such as, e.g., steels or engineering ceramics, that allow many molding cycles and, in the process, always meet the requirements in respect of the given tolerances. In the case of an injection molding method, the polymer granulate is initially thermally liquefied and pressed through a hot runner into the injection mold at a high pressure (approximately 500 to 2000 bar). During injection and cooling, the pressure-temperature regime is decisive for the optical properties of such a lens element, in particular for the stability and homogeneity of the optical properties.

Regarding the material properties when using an optical polymer for a lens element according to the invention or a contact apparatus according to the invention, it is advantageous for example if:
the optical polymer has a water absorption of less than or equal to 0.2%, for example less than or equal to 0.1%, and/or
the refractive index of the optical polymer has an inhomogeneity within the optical zone of less than or equal to +/−0.01, for example of less than or equal to +/−0.002, and/or
the refractive index of the optical polymer after processing has a climate-related variation of less than or equal to +/−0.02, for example of less than or equal to +/−0.01.

It may also be beneficial if the optically effective zone of the lens element after processing has a birefringence of less than or equal to +/−0.01, for example of less than or equal to +/−0.005.

If the optically effective zone of the lens element is made from an optical polymer, it is advantageous if differences in the refractive index of the optical polymer to the refractive index of mineral glass are compensated for by adapting the shape and/or thickness of the optically effective zone of the lens element.

A lens element according to the invention or a contact apparatus according to the invention for which the eye-side boundary surface of the optically effective zone of the lens element is adapted to the curvature of the cornea of the patient's eye may be preferred. Ideally, the curvature of the eye-side boundary surface of the lens element then has a somewhat larger radius than the radius of the corneal surface. Due to the curvature of the eye-side boundary surface of the lens element, a strong pressure on the cornea of the patient's eye is avoided; the adaptation of the radius of curvature prevents the occurrence of bubbles between the lens element and the cornea of the patient's eye.

In a first embodiment of the lens element according to the invention or the contact apparatus according to the invention, the device-side boundary surface of the optically effective zone of the lens element is designed to be planar.

In a second special embodiment, the device-side boundary surface of the optically effective zone of the lens element is designed to be curved. The curvature of the device-side boundary surface here for example has a radius of greater than 0.1 m and in another example a radius of greater than 1 m. In particular for a polymer lens element whose eye-side boundary surface is shaped like in the case of a lens element made from mineral glass, this offers the possibility of adapting the lens properties to the properties of a lens element made from mineral glass.

In a third special embodiment, the device-side boundary surface of the optically effective zone of the lens element has an aspherical shape. Such shapes are advantageous for example in particular for lens elements made from an optical polymer.

In a particular embodiment of the lens element according to the invention or the contact apparatus according to the invention, the lens element has a contact surface of the joining zone that circumferentially extends around the device-side boundary surface over the entire periphery, wherein the circumferential contact surface for example furthermore has a step to the device-side boundary surface of the optically effective zone. Such an embodiment allows uncomplicated, direct contact between the lens element of the contact apparatus and the laser applicator of the ophthalmological laser therapy system. The formation of such an "additional" zone at the lens element also serves here—in addition to good contact—to avoid stresses in the optically effective zone of the lens element. An additional step furthermore allows better alignment—in particular in the lateral direction.

The device-side boundary surface thus has a central zone, which is the optically effective zone and can be planar or curved, and a joining zone surrounding said central zone in the shape of a ring and possibly a functional zone, which is formed as a contact surface for being received at the objective of the laser applicator or in the laser applicator.

This contact surface can now have a special design: A plane-parallel embodiment to a laser applicator interface, with a smooth surface or with a specially structured surface that matches in particular the laser applicator interface, which allows a force-fitting or form-fitting connection to be made to the laser applicator, may be advantageous.

It may also be advantageous for a lens element according to the invention or a contact apparatus according to the invention if the joining zone of the lens element has a circumferential bevel to the device-side boundary surface of the lens element, in particular a bevel with a width greater than or equal to 0.05 mm. In an alternative advantageous refinement, the joining zone of the lens element, possibly in particular its functional zone, has rounded edges. This makes it easier to distribute the stress peaks in the material.

A special embodiment of the lens element according to the invention or the contact apparatus according to the invention has,
   in a first alternative, no anti-reflective coating, neither on the device-side boundary surface of the optically effective zone nor on the eye-side boundary surface of the optically effective zone of the lens element, or,
   in a second alternative, an anti-reflective coating on the device-side boundary surface of the optically effective zone, but no anti-reflective coating on the eye-side boundary surface of the optically effective zone of the lens element.

Working without an anti-reflective coating may offer a number of advantages: The costs are lower because an anti-reflective coating requires high production costs. Such a lens element or such a contact apparatus is less prone to errors, since adhesion problems can arise, in particular for a lens element made from a polymer, and an anti-reflective coating is technologically not absolutely necessary: Any loss of energy that may occur can be compensated for by increasing the laser energy.

In a method according to the invention for producing a lens element described above, in a first alternative, the optically effective zone and the functional zone of the joining zone are produced in one step, and thus in a single piece, by use of an injection molding method.

In a second alternative of the method according to the invention for producing a lens element described above, the optically effective zone of the lens element is first produced and then the functional zone of the joining zone is added, for example by application of an injection molding method.

In a method according to the invention for producing a contact apparatus described above, a lens element is first manufactured, for example using one of the above-described methods for producing the lens element, and then
   the holding device is produced by use of a 2-component injection molding method or overmolding and is permanently connected to the lens element, or
   the holding device is produced by use of an injection molding method and is permanently connected to the lens element by laser welding or ultrasonic welding, click connection, or pressing connection.

Such an inventive method for producing a contact apparatus for example comprises one or more optical inline inspections during an automated production process.

It is understood that the features specified above and the features yet to be explained below can be used not only in the specified combinations, but also in other combinations or on their own, without departing from the scope of the present invention.

The invention is explained in even greater detail below for example with reference to the accompanying drawings, which also disclose features essential to the invention.

DETAILED DESCRIPTION

Figure 1:
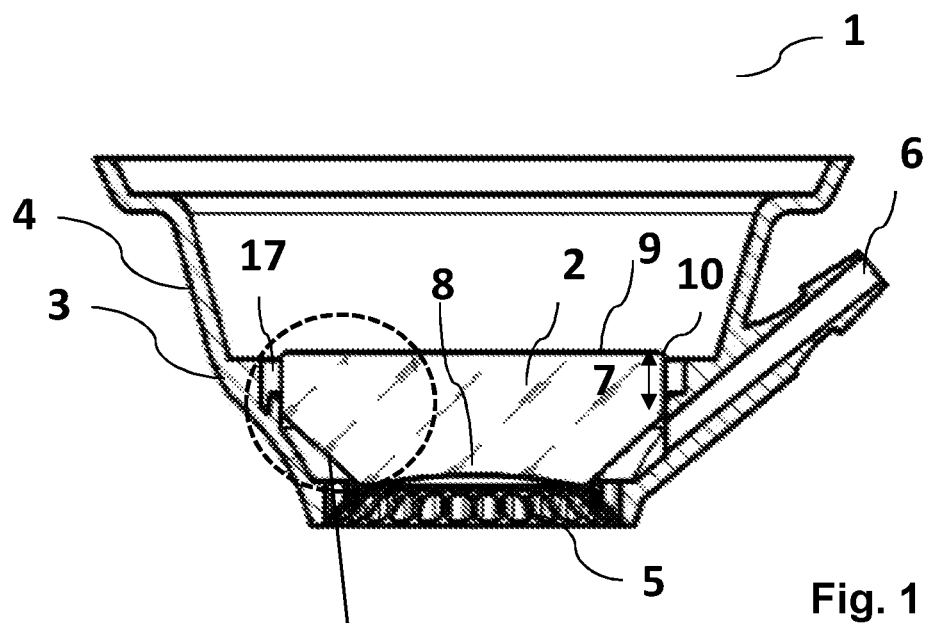
FIG. 1 is a cross-sectional view of a contact apparatus having a lens element according to an example embodiment of the invention.
Figure 1A:
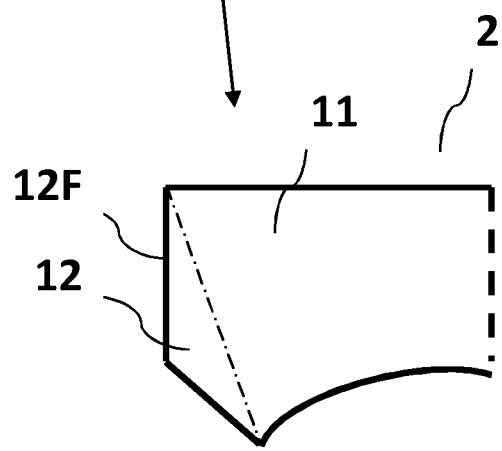
FIG. 1A is a partial cross sectional view of a lens element as depicted in FIG. 1.

FIG. 1 shows a contact apparatus 1 having a lens element 2 for direct contact with the corneal surface of a patient's eye A1 and a frustoconical holding device 3 having a wall 4, a suction element 5 in the lower region of the holding device 3, and a vacuum feed-through 6 that can be connected to a discharge line to a pump element, according to the prior art. The lens element 2 is made from a mineral glass, here a quartz glass. It has a periphery 10, wherein the thickness 7 of the circumferential peripheral region is greater than zero. The lens element has a planar device-side boundary surface 9 and a curvature of the eye-side boundary surface 8 of the lens element 2 that is adapted to the curvature of the corneal surface of the patient's eye A1. The optically effective zone 11 extends over the entire device-side boundary surface of the lens element 2. FIG. 1a shows an enlarged section of the lens element 2, in which the course of the optically effective zone 11 becomes clear in a partial section of the lens element 2. This optically effective zone 11 is usually adjacent to a joining zone 12 having a joining surface 12F. The contact to the holding device 3 is established via the joining surface 12F, which usually extends only over a partial region of the periphery of the lens element 2, specifically in the lower region of the lens periphery, wherein the lens element 2 is adhesively bonded to the holding device 3 along said joining surface 12F in accordance with the prior art. However, the lengthy adhesive-bonding process does not cause the joining zone 12 to change itself in terms of the optical and mechanical properties thereof.

Figure 2:
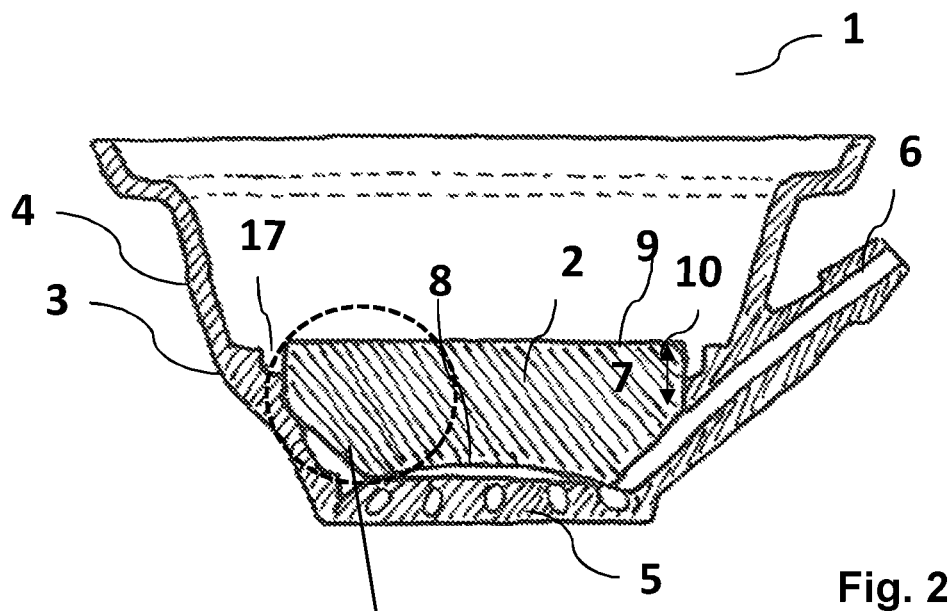
FIG. 2 is a cross-sectional view of a contact apparatus having a lens element according to an example embodiment of the invention.
Figure 2A:
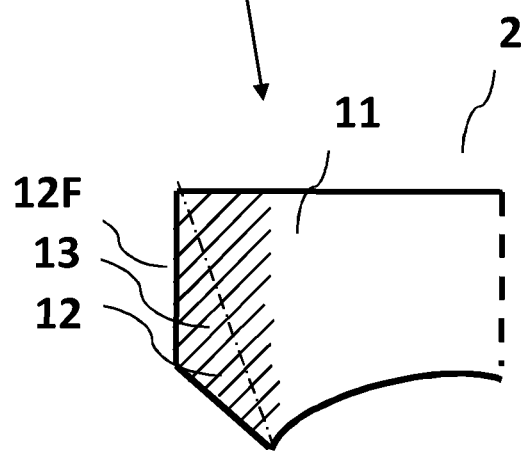
FIG. 2A is a partial cross sectional view of a lens element as depicted in FIG. 2.

FIG. 2 shows a contact apparatus 1 in the same situation as in FIG. 1, only that the lens element 2 is made from an optical polymer. A laser welding process was used to connect the lens element 2 to the holding device 3 of the contact apparatus 1. The effect of the laser welding is shown in the enlarged section of the lens element 2 in FIG. 2a. A change zone 13, in which the mechanical and especially the optical properties of the lens element 2 were subsequently changed by the laser welding process and which extends not only over the joining zone 12 but also far into the optically effective zone 11, was produced by the laser welding process, now restricting the optically usable zone of the entire optically effective zone 11 of the lens element 2. This must be avoided.

Figure 3:
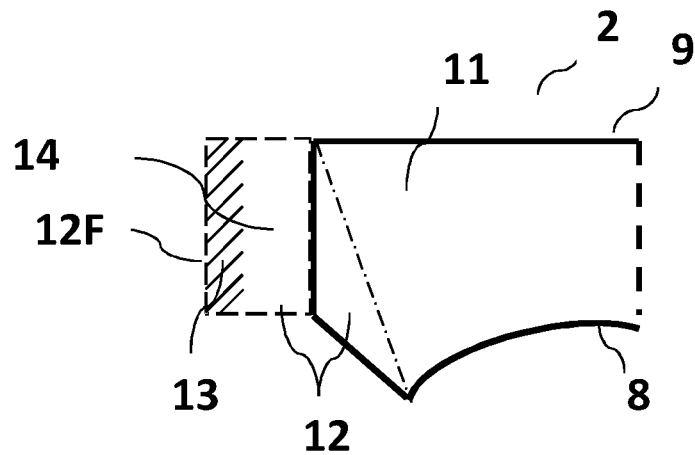
FIG. 3 is a partial cross sectional view of a lens element according to an example embodiment of the invention.

FIG. 3 shows a section of a first example embodiment of a lens element 2 according to the invention with a functional zone 14 that makes possible a joining method for the permanent connection between the lens element 2 and the holding device 3 that is not an adhesive-bonding method: In this first example embodiment, the functional zone 14 is realized by a joining contact zone, an additional structure, with a cuboid cross section, surrounding the lens element 2, in which the region close to the joining surface 12F is changed optically and mechanically during the joining method, in the present case by overmolding or a pressing connection. In this case, however, the optically effective zone 11 is not affected.

Figure 4:
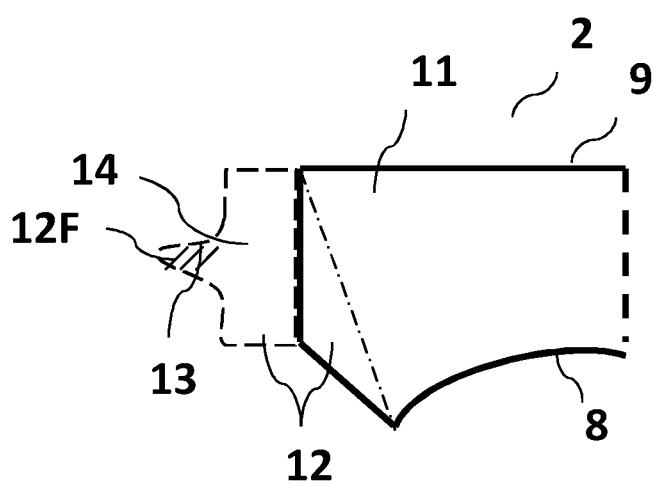
FIG. 4 is a partial cross sectional view of a lens element according to an example embodiment of the invention.

FIG. 4 shows a section of a second example embodiment of a lens element 2 according to the invention with a functional zone 14 that makes possible a joining method for the permanent connection between the lens element 2 and the holding device 3 that is not an adhesive-bonding method: In this second example embodiment, the functional zone 14 is realized by an additional structure, with a cuboid cross section and a melt lip, surrounding the lens element 2. The joining surface 12F, which is initially very small here, and in particular the region close to the joining surface, is changed optically and mechanically during the joining method, in the present case by a laser welding method or an ultrasonic welding method. During the welding process, even part of the melt lip of the functional zone 14 is "consumed" here. In this case too, however, the optically effective zone 11 is not affected, and its properties are not changed.

Figure 5:
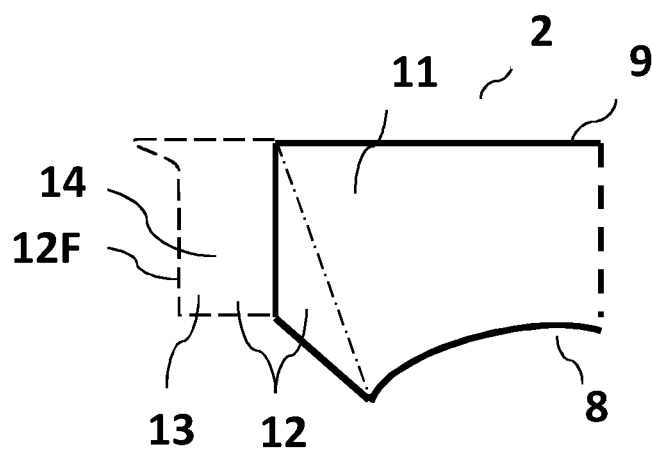
FIG. 5 is a partial cross sectional view of a lens element according to an example embodiment of the invention.

FIG. 5 shows a section of a third example embodiment of a lens element 2 according to the invention with a functional zone 14, which makes possible a joining method for the permanent connection between the lens element 2 and the holding device 3 that is not an adhesive-bonding method: In this third example embodiment, the functional zone 14 is realized by an undercut for effecting a click connection and an additional structure, with a cuboid cross section, surrounding the lens element 2. The optically effective zone 11 is not changed during the joining process in this case either.

Figure 6:
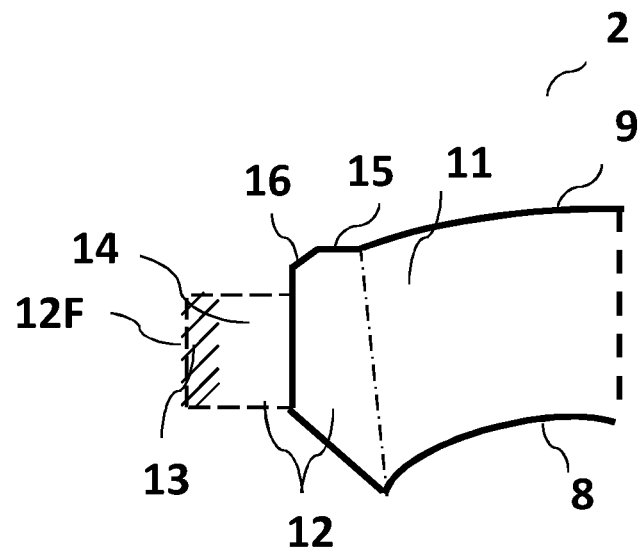
FIG. 6 is a partial cross sectional view of a lens element according to an example embodiment of the invention.

FIG. 6 shows a section of a fourth example embodiment of a lens element 2 according to the invention with a changed joining zone 12 and optionally with a functional zone 14 that makes possible a joining method for the permanent connection between the lens element 2 and the holding device 3 that is not an adhesive-bonding method. The part of the joining zone 12 of the lens element 2 itself is embodied to be wider than in the previous example embodiments. It makes possible an (additional) contact surface 15 for being received in the objective of the laser applicator, via which direct contact and a corresponding connection to the laser applicator is made possible, while in this fourth example embodiment, the device-side boundary surface 9 of the lens element 2 is curved in the region of the optically effective zone 11. While in the previous example embodiments of a lens element 2 according to the invention this may be carried out equally with a mineral glass and with an optical polymer, the lens element 2 in the fourth example embodiment is for example made from an optical polymer, since this is much easier to manufacture than such a structure made from a mineral glass. A circumferential bevel 16 of the joining zone 12 additionally avoids stress peaks and makes it easier to handle the contact glass when it is connected to the laser applicator.

The optional functional zone 14 is realized in this fourth example embodiment by a joining contact zone, an additional structure, with a cuboid cross section, surrounding the lens element 2, in which the region close to the joining surface 12F is changed optically and mechanically during the joining method. The optically effective zone 11 is again not affected by this.

Figure 7:
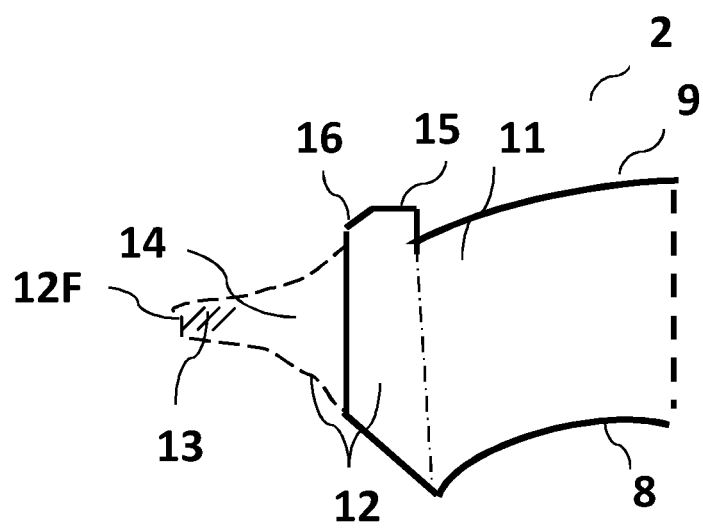
FIG. 7 is a partial cross sectional view of a lens element according to an example embodiment of the invention.

FIG. 7 shows a section of a fifth example embodiment of a lens element 2 according to the invention with a changed joining zone 12 and optionally with a functional zone 14 that makes possible a joining method for the permanent connection between the lens element 2 and the holding device 3 that is not an adhesive-bonding method. The part of the joining zone 12 of the lens element 2 itself is again embodied to be wider than in the first to third example embodiments. In addition, it has a step that allows easy alignment with the laser applicator of the ophthalmological laser therapy system 100. The wider joining zone 12 of the lens element 2 makes possible a contact surface 15 for being received in the objective of the laser applicator, via which a direct contact and a corresponding connection to the laser applicator is made possible. The step of the contact surface 15 opposite the device-side boundary surface 9 is smaller than 3 mm, for example smaller than 1 mm. It allows simpler manufacturing of the lens element 2 and/or improves its handling, inter alia, during manufacture. In this fifth example embodiment, the device-side boundary surface 9 of the lens element 2, which is again for example made from an optical polymer, is designed to be curved in the region of the optically effective zone 11. A circumferential bevel 16 of the joining zone 12 again avoids stress peaks and makes handling by the user easier.

The optional functional zone 14 in this fifth example embodiment is realized by a functional zone 14 with a melt lip, in which the region that is close to the joining surface 12F is changed optically and mechanically during the joining method. The optically effective zone 11 is again not affected by this.

Figure 8:
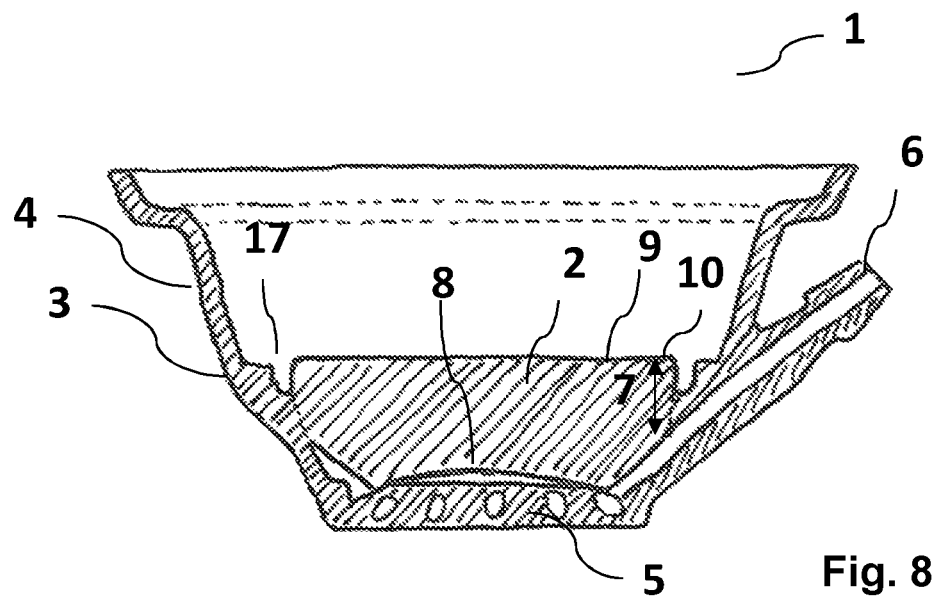
FIG. 8 is a cross-sectional view of a contact apparatus having a lens element according to an example embodiment of the invention.

FIG. 8 now shows a first contact apparatus 1 according to the invention with a lens element 2 made from an optical polymer, which was connected to a holding device 3, also made from a polymer, by application of overmolding with the aid of a functional zone 14 in the form of a joining contact zone—here with the consumption of the joining contact zone.

Figure 9:
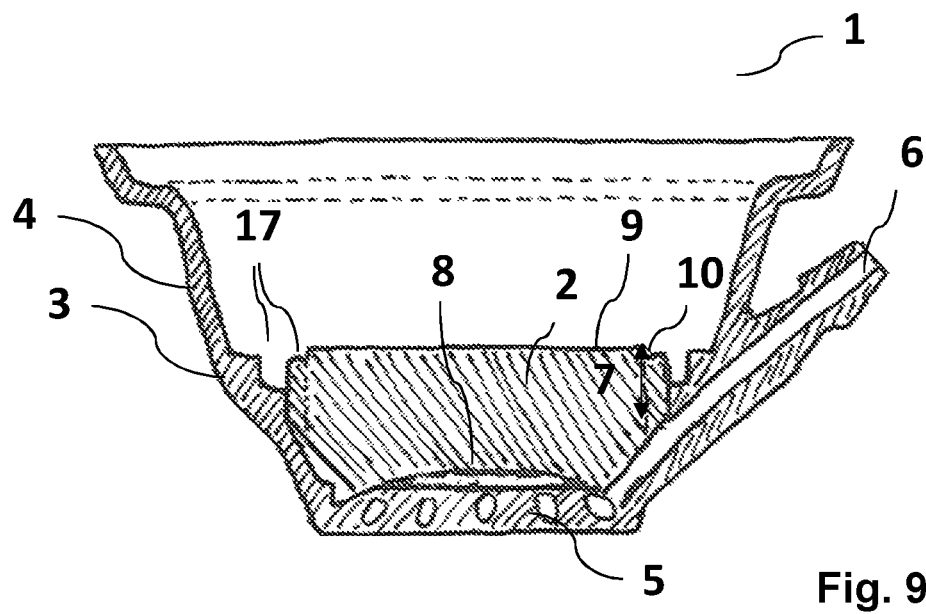
FIG. 9 is a cross-sectional view of a contact apparatus having a lens element according to an example embodiment of the invention.

FIG. 9, by contrast, shows a second contact apparatus 1 according to the invention with a lens element 2 made from an optical polymer, which was connected to a holding device 3, also made from a polymer, by use of a pressing connection with the aid of a functional zone 14, again in the form of a joining contact zone. In this case, the joining contact zone absorbs the stresses that arise in the process, with the result that the optically effective zone 11 of the lens element 2 is not influenced thereby.

Figure 10:
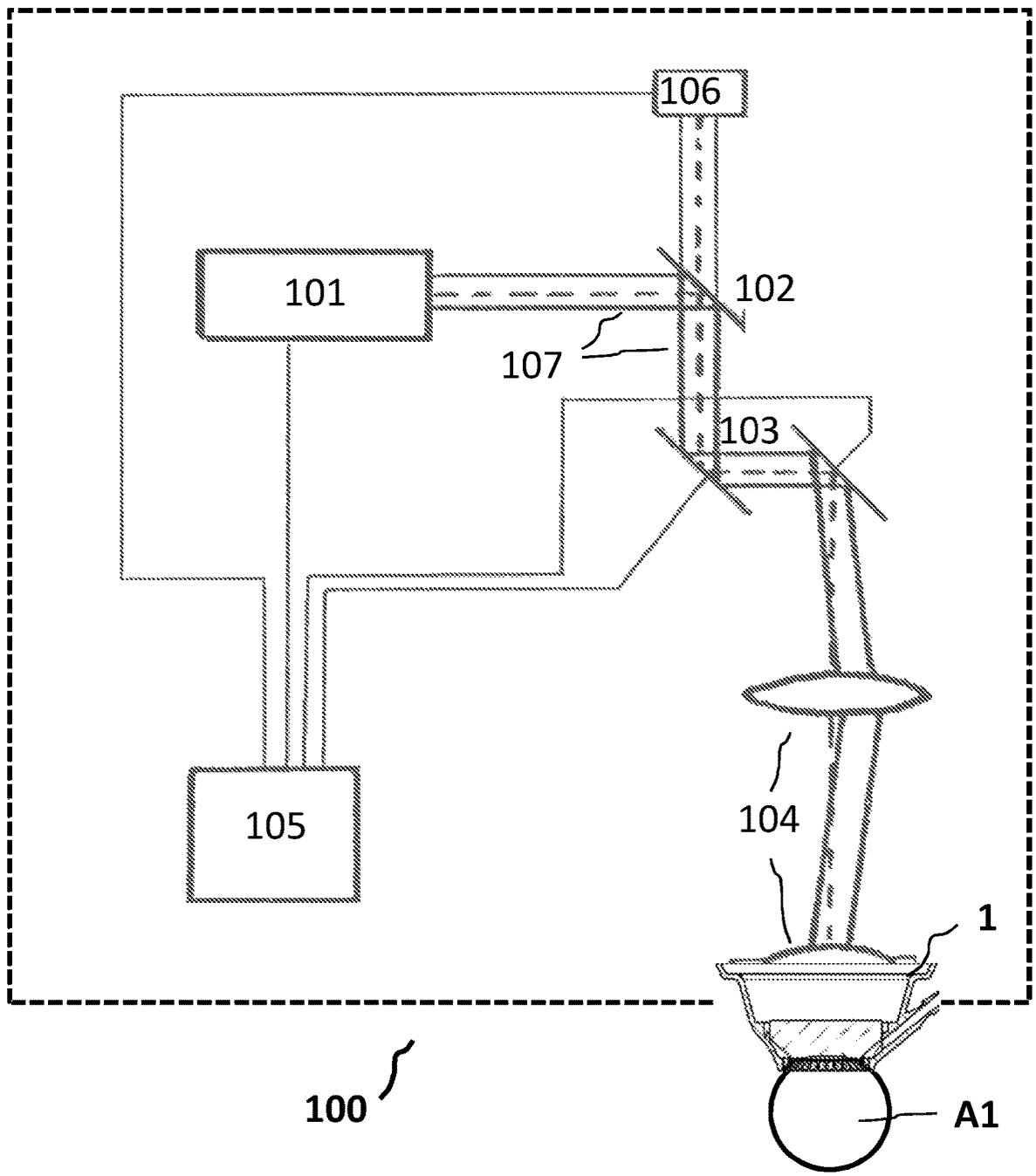
FIG. 10 is a schematic depiction of a contact apparatus and a therapeutic ophthalmic laser apparatus and an eye according to an example embodiment of the invention.

FIG. 10 shows a schematic overall view of an embodiment of the ophthalmological laser therapy system 100 with a contact apparatus 1 according to the invention. The details of such a laser therapy system 100 will not be discussed here. FIG. 10 serves only to show, using the example of such a system, how an eye A1 is fixed at the ophthalmological laser therapy system 100 by application of a contact apparatus 1 according to the invention and thus how the relative geometric position of an eye A1 with respect to an ophthalmological laser therapy system 100 is determined. The laser therapy system here contains a laser 101, for example a femtosecond laser, the beam of which is directed through a beam splitter 102 to a scanning unit 103 that contains two scanning mirrors mounted so as to be rotatable about two mutually perpendicular axes of rotation. This allows the laser beam to be deflected two-dimensionally. The beam is guided further onto the eye A1 via a focusing and projection optical unit 104 containing two lenses (in this example). In this example, part of the beam is then scattered back by the cornea of the eye A1, passes through the beam splitter 102, and is detected by the detector 106. A control unit 105 evaluates the data supplied by the detector 106 and controls the laser 102, the scanning unit 103, and the projection optical unit 104. Since the position of the eye A1 in relation to the laser therapy system 100 is now fixed by the contact apparatus 1, it is ensured that, for example in a laser surgical application, laser radiation that leaves the ophthalmological laser therapy system 100 can act at the intended location on the eye A1 and that signals that are received by the eye A1 in the ophthalmological laser therapy system can be uniquely assigned to a location on the eye A1. This is shown by the schematic beam path 107 within the ophthalmological laser therapy system 100.

The above-mentioned features of the invention, which are explained in various example embodiments, can be used not only in the combinations specified in an example manner but also in other combinations or on their own, without departing from the scope of the present invention.

A description of an apparatus relating to method features is analogously applicable to the corresponding method with respect to these features, while method features correspondingly represent functional features of the apparatus described.

The invention claimed is:

1. A lens element for a contact apparatus that fixes the relative geometric position of a patient's eye with respect to a laser applicator of an ophthalmological laser therapy system, the lens element comprising:
   an optically effective zone; and
   a joining zone having a joining surface;
   wherein the joining zone of the lens element further comprises a functional zone that facilitates joining the lens element into a holding device, the functional zone being arranged continuously circumferentially or discontinuously circumferentially at the outer periphery of the lens element;
   wherein the functional zone comprises a consumption zone in which material is removed or changed in optical and mechanical properties thereof in a subsequent joining process; and
   wherein the functional zone is joined with the optically effective zone and the optically effective zone is not affected during the joining process of the functional zone.

2. The lens element as claimed in claim 1, wherein the functional zone comprises at least one of the following:
   a joining contact zone adapted for remelting or adapted for injection molding;
   a melt lip adapted for laser welding or adapted for ultrasonic welding; or
   an undercut that facilitates effecting a click connection.

3. The lens element as claimed in claim 1, wherein
   the optically effective zone and the functional zone of the lens element are made in a single piece from a mineral glass, or
   wherein the optically effective zone and the functional zone of the lens element are made from a polymer, or
   wherein the optically effective zone of the lens element is made from a mineral glass and the functional zone of the lens element is made from a polymer.

4. The lens element as claimed in claim 1, wherein the optically effective zone and the functional zone of the lens element are made from a polymer and in a single piece.

5. The lens element as claimed in one of claim 1, wherein the lens element comprises a part of a holding device.

6. The lens element as claimed in one of claim 5, wherein the holding device, comprises a suction element.

7. A contact apparatus that fixes the relative geometric position of a patient's eye to a laser applicator of an ophthalmological laser therapy system, comprising:
   a lens element according to claim 1 and a holding device, which are permanently connected to one another, with the result that the contact apparatus is made in one piece, and
   wherein the holding device comprises a wall, a lower suction element and a vacuum feed-through, wherein the vacuum feed-through extends through the wall into the suction element, and
   wherein the lens element and the holding device are not permanently connected to one another by an adhesive-bonding.

8. The contact apparatus as claimed in claim 7, wherein the lens element is permanently connected to the holding device by one of the following: 2-component injection molding, overmolding, a laser weld or an ultrasonic weld, a click connection and a pressing connection.

9. The contact apparatus as claimed in claim 7, wherein the lens element and holding device are made from one or more materials
   that do/does not include any substances that have a hormonal or hormone-like effect on the human organism, and/or
   that are biocompatible.

10. The contact apparatus as claimed in claim 7, wherein the lens element is formed in a single piece.

11. The contact apparatus as claimed in claim 7, wherein the lens element and the holding device are manufactured additively.

12. The lens element as claimed in claim 1, wherein the optically effective zone, the functional zone or both is at least one of the following:
    made from an optical polymer that has a refractive index close to that of mineral glass or has a refractive index of between 1.4 and 1.55 for a wavelength of therapy laser radiation;
    injection molded; and
    made of at least one of the following polymers: polycarbonate, polystyrene, polymethyl methacrylate, cycloolefin polymers, cycloolefin copolymers, polyetherimide, polyethylene terephthalate, polysulfone.

13. The lens element as claimed in claim 1, wherein at least one of the following is true:
    the optical polymer has a water absorption of less than or equal to 0.2%;
    the optical polymer has a water absorption of less than or equal to 0.1%;
    the refractive index of the optical polymer has an inhomogeneity within the optical zone of less than or equal to +/−0.01;
    the refractive index of the optical polymer has an inhomogeneity within the optical zone of less than or equal to +/−0.002;
    the optically effective zone of the lens element after processing has a birefringence of less than or equal to +/−0.01;
    the optically effective zone of the lens element after processing has a birefringence of less than or equal to +/−0.005;
    the refractive index of the optical polymer after processing has a climate-related variation of less than or equal to +/−0.02; and
    the refractive index of the optical polymer after processing has a climate-related variation of less than or equal to +/−0.01.

14. The lens element as claimed in claim 1, wherein the optically effective zone of the lens element is made from an optical polymer and compensated for differences in a refractive index of the optical polymer to a refractive index of mineral glass by adapting a shape and/or a thickness of the optically effective zone of the lens element.

15. The lens element as claimed in claim 1, wherein at least one of the following is true:
    a device-side boundary surface of the optically effective zone is planar;
    the device-side boundary surface of the optically effective zone is curved;
    the curvature of the device-side boundary surface has a radius of greater than 0.1 m;
    the curvature of the device-side boundary surface has a radius of greater than 1 m; and
    the device-side boundary surface of the optically effective zone has an aspherical shape.

16. The contact apparatus as claimed in claim 7 wherein at least one of the following is true:
    a device-side boundary surface of the optically effective zone is planar;
    the device-side boundary surface of the optically effective zone is curved;
    the curvature of the device-side boundary surface has a radius of greater than 0.1 m;
    the curvature of the device-side boundary surface has a radius of greater than 1 m; and
    the device-side boundary surface of the optically effective zone has an aspherical shape.

17. The lens element as claimed in claim 1, wherein at least one of the following is true:
    the lens element has a contact surface of the joining zone that circumferentially extends around the device-side boundary surface over an entire periphery; and
    the circumferential contact surface has a step to the device-side boundary surface of the optically effective zone.

18. The lens element as claimed in claim 1, wherein at least one of the following is true:
    the joining zone has a circumferential bevel to the device-side boundary surface of the lens element;
    the circumferential bevel has a width greater than or equal to 0.05 mm;
    the joining zone has rounded edges; and
    the functional zone has rounded edges.

19. The lens element as claimed in claim 1,
    wherein the lens element has no anti-reflective coating, neither on the device-side boundary surface of the optically effective zone nor on the eye-side boundary surface of the optically effective zone of the lens element, or
    wherein the lens element has an anti-reflective coating on the device-side boundary surface of the optically effective zone, but no anti-reflective coating on the eye-side boundary surface of the optically effective zone of the lens element.

* * * * *

UNITED STATES PATENT AND TRADEMARK OFFICE
CERTIFICATE OF CORRECTION

PATENT NO. : 12,099,259 B2
APPLICATION NO. : 17/271862
DATED : September 24, 2024
INVENTOR(S) : Preuss et al.

It is certified that error appears in the above-identified patent and that said Letters Patent is hereby corrected as shown below:

In the Specification

Column 3, Line 50, delete "is may" and insert --may--

Column 5, Line 48, delete "wavelengths, in turn" and insert --wavelengths--

Column 6, Line 2, delete "tomograph" and insert --tomography--

In the Claims

Column 14, Line 36, Claim 5 delete "in one of" and insert --in--

Column 14, Line 38, Claim 6 delete "in one of" and insert --in--

Signed and Sealed this
Twenty-seventh Day of January, 2026

John A. Squires
*Director of the United States Patent and Trademark Office*